(12) United States Patent
Tung

(10) Patent No.: US 6,997,553 B2
(45) Date of Patent: Feb. 14, 2006

(54) CONTACT LENS FOR RESHAPING THE ALTERED CORNEAS OF POST REFRACTIVE SURGERY, PREVIOUS ORTHO-K OF KERATOCONUS

(75) Inventor: Hsiao-Ching Tung, Taipei (TW)

(73) Assignee: Global-Ok Vision, Inc., Tortola (VG)

( * ) Notice: Subject to any disclaimer, the term of this patent is extended or adjusted under 35 U.S.C. 154(b) by 0 days.

(21) Appl. No.: 10/895,692

(22) Filed: Jul. 20, 2004

(65) Prior Publication Data

US 2004/0257524 A1      Dec. 23, 2004

Related U.S. Application Data

(63) Continuation of application No. PCT/US03/24624, filed on Aug. 6, 2003, which is a continuation of application No. 10/214,652, filed on Aug. 7, 2002, now Pat. No. 6,652,095.

(51) Int. Cl.
G02C 7/04        (2006.01)
(52) U.S. Cl. .................. 351/160 R; 351/161; 351/177

(58) Field of Classification Search ............ 351/160 H, 351/160 R, 161, 162, 177
See application file for complete search history.

(56) References Cited

U.S. PATENT DOCUMENTS 5,695,509 A  *  12/1997   El Hage  ..................... 606/166

* cited by examiner

*Primary Examiner*—Scott J. Sugarman
(74) *Attorney, Agent, or Firm*—East I.P. Group; Philip K. Yu

(57) ABSTRACT

A contact lens is fitted to a cornea of a patient's eye to gradually alter the patient's cornea during continued wear to reshape the altered cornea conditions such as the corneas of post refractive surgery, post previous Ortho-K. and keratoconus. The contact lens has a plurality of zones that comprise one optical zone, at least one conformation zone, a connecting zones complex, an alignment zone and a peripheral zone. The one or more conformation zones are utilized to conform the angle of the central optical zone, as well as the alignment zone, to compress on the central and mid-peripheral portion of the altered cornea for redistribute cornea tissue to reduce the residual refractive errors, after refractive surgery, or to smooth out the central cornea surface of the keratoconus for better bare or spectacle vision after contact lens are removed.

34 Claims, 6 Drawing Sheets

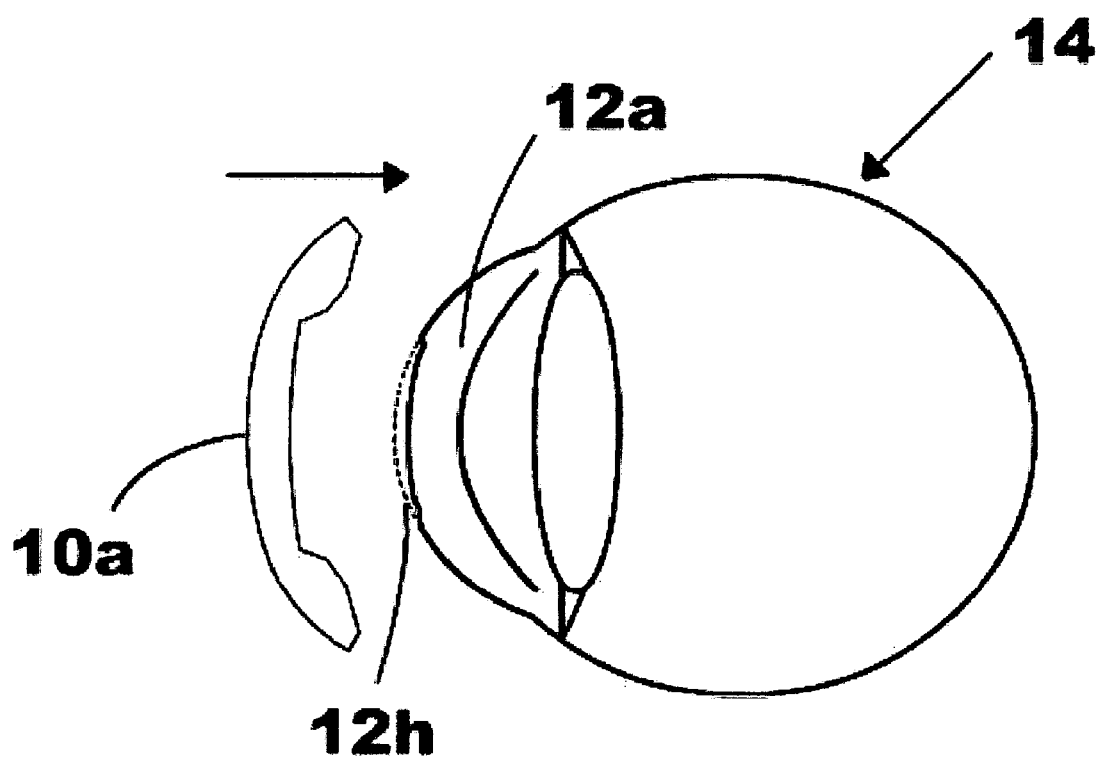

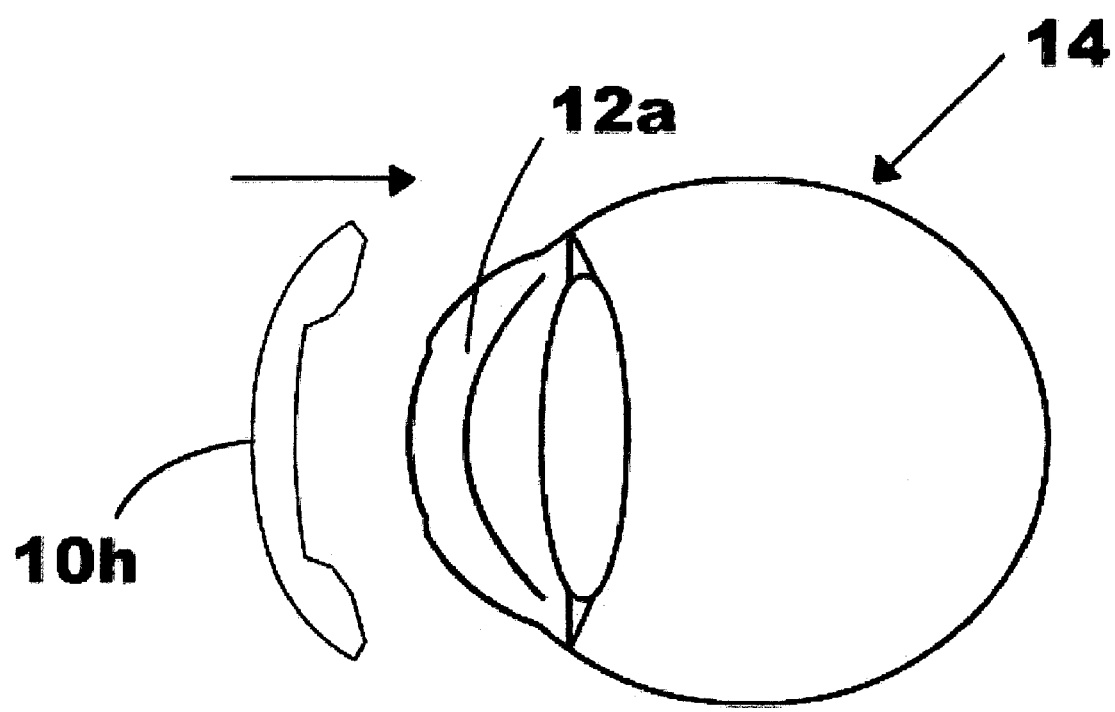

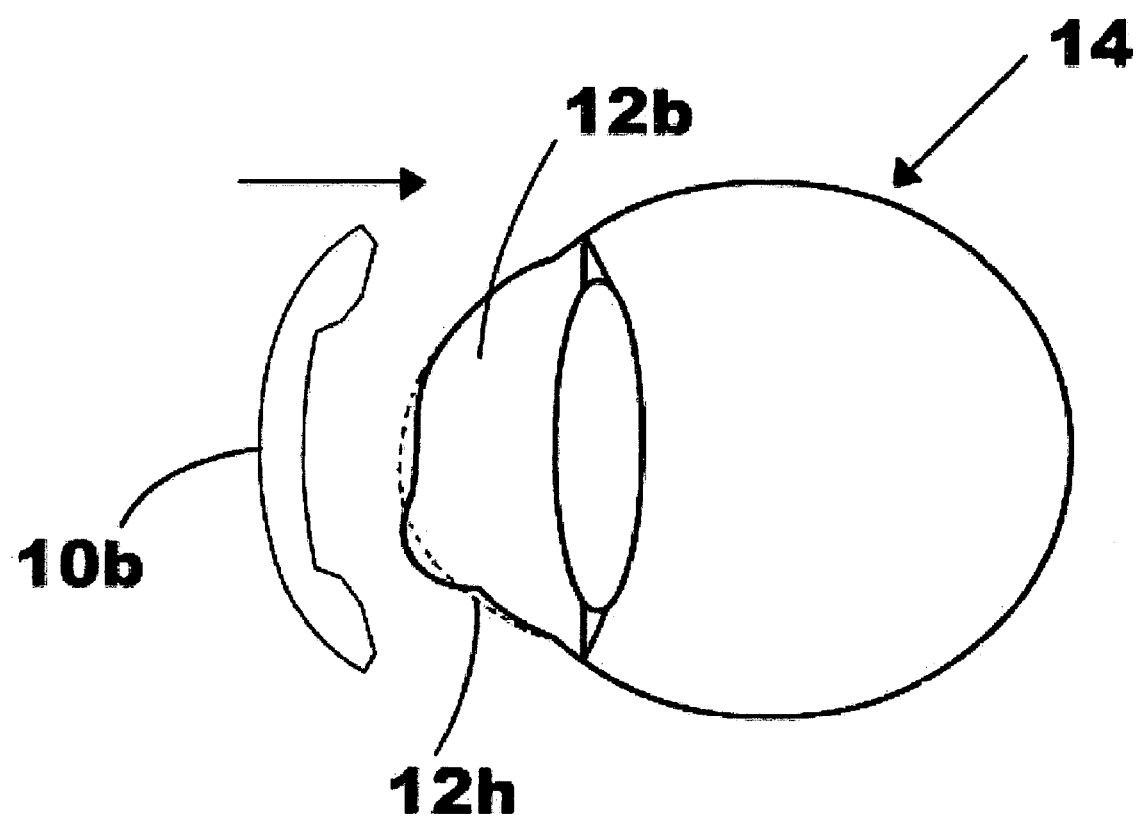

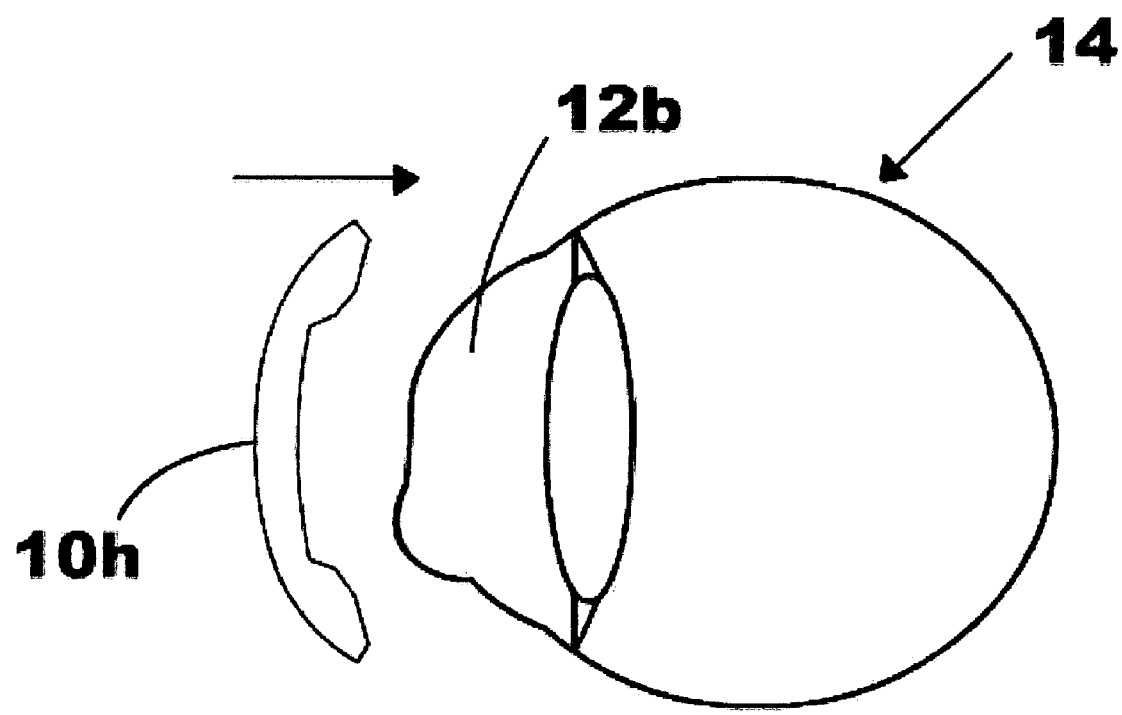

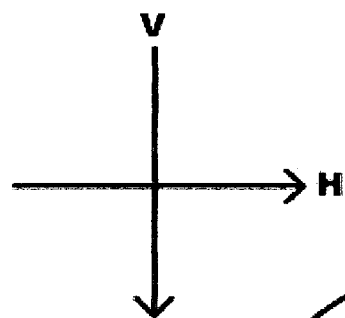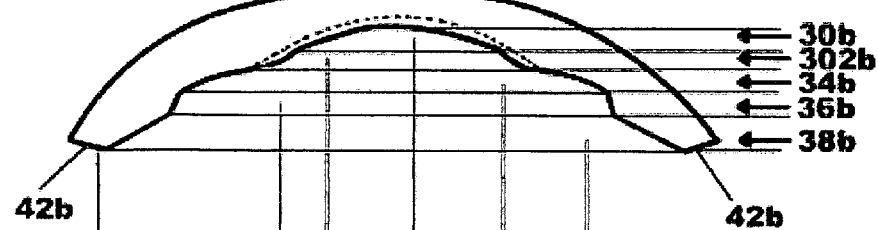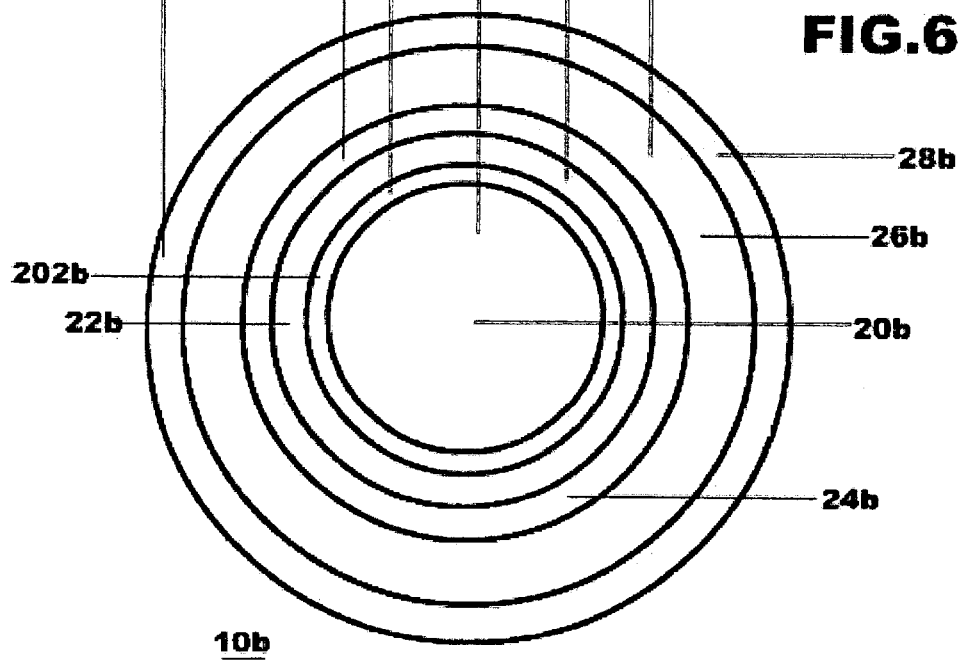

CONTACT LENS FOR RESHAPING THE ALTERED CORNEAS OF POST REFRACTIVE SURGERY, PREVIOUS ORTHO-K OF KERATOCONUS

RELATED APPLICATION

The present application is a continuation of a Patent Cooperation Treaty International application, filed on Aug. 6, 2003, to the United States Receiving Office, with International Application No. PCT/US03/24624, which is a continuation of a U.S. application, filed on Aug. 7, 2002, with application Ser. No. 10/214,652, now U.S. Pat. No. 6,652, 095. The entire disclosure of the PCT and US applications are incorporated by this reference as though set forth fully herein.

BACKGROUND OF THE INVENTION

1. Field of the Invention

The present invention relates to contact lenses for reshaping corneas, and more particularly relates to contact lenses for reshaping altered corneas which are geometrically abnormal, such as post-refractive surgical corneas for the enhancement of residual myopia, for eliminating over-treated hyperopia and/or presbyopia, and for reshaping irregular corneas such as advanced or severe Keratoconus to restore usable spectacle vision. More particularly, the invention relates to contact lenses that are shaped to provide gradual altering of the patient's cornea during continued wear to reshape the cornea to eliminate the residual myopia, hyperopia, presbyopia, or astigmatism of altered cornea condition. The lens may also be adapted for enhancement of previously Ortho-K altered corneas for adding on myopia reduction.

2. Art Background

Many people experience difficulties with their vision due to a number of possible conditions. The most common vision problem is a condition known as myopia or near-sightedness. Myopia is a common condition where an eye cannot focus on far-away objects because the cornea of the eye is curved too steeply (i.e., where the radius of curvature of the cornea is smaller than normal) to provide adequate focusing at the retina of the eye.

Another condition is known as hyperopia or farsightedness. With hyperopia, the eye cannot focus on both far and near objects because the curvature of the cornea of the eye is too flat (i.e., where the radius of curvature of the cornea is larger than normal) to provide adequate focusing at the retina of the eye. Hyperopia is common among young children. Severe hyperopia will induce lazy eye or amblyopia in childhood. Mild or moderate hyperopia is tolerable and insidious in young ages but will cause reading problems in older age.

Yet, another common problem is astigmatism, where unequal curvature of one or more refractive surfaces of the cornea prevents light rays from focusing clearly at one point on the retina, resulting in blurred vision. Presbyopia is the most common vision problem in adults 40 years and older. It does not matter whether they are emmetropic (normal condition), myopic or hyperopic in far vision, the middle-aged population, i.e. over 40 years old, will begin to experience difficulty in focusing on close objects, due to the loss of flexibility of the eye's crystalline lens. Presbyopia may occur and complicate other refractive problems such as hyperopia, myopia or astigmatism.

A normal cornea is usually parabolic in shape, which is steepest (shorter radius) in curvature at, or nearly at, the central portion of the cornea and becomes progressively flatter (longer radius) in curvature to the limbus by certain positive e-value, or so-called "positive shape factor. An altered cornea is a cornea that is far different from the normal parabolic shape, having an abruptly protruded portion or a "negative shape factor" of a human cornea, which may occur naturally, or results from some refractive surgical procedures.

The former condition, i.e. "naturally altered," is best demonstrated by Keratoconus, which is manifested by an abruptly protruded cone that is usually located slightly inferior (i e. lower portion of) to the cornea. It would be difficult to obtain useful vision in advanced or severe Keratoconus by spectacles or any type of contact lenses. The final choice to restore useful vision will be cornea transplantation traditionally. However, complications accompanying cornea transplantation are very common such as irregular astigmatism, graft rejection, infection or recurrence of Keratoconus. That's the reason why any non-surgical method that may rehabilitate Keratoconus and avoid cornea transplantation will be quite valuable.

The latter condition, i.e. due to surgical procedures, is best illustrated by the myopic refractive surgery such as LASIK, PRK and RK. The post-operative cornea is usually manifested by an ablated, flattened curvature at the center portion of the cornea. It is not uncommon to still have unsatisfactory vision, even after the refractive surgery, such as residual myopia, over-corrective hyperopia, iatrogenic Keratoconus or irregular astigmatism. The usual ways to manage the post-operative complications are enhancement operations, wearing glasses, fitting contact lenses or cornea transplantation for the severe cases.

Another conventional approach to treating some or all of these refractive errors is to alter the corneal shape by wearing contact lenses which are designed to continually exert pressure on selected locations of the cornea to gradually force or mold the cornea into the desired corneal curvature. A retainer lens is then worn on a part-time basis to prevent the cornea from returning to its previously deformed shape. This method of treatment is commonly referred to as orthokeratology (referred to hereinafter as "Ortho-K"). While Ortho-K is traditionally applied to the normal corneas to correct myopia, astigmatism and hyperopia, its application to the altered corneas has been unexplored, since it is considered very difficult to figure out a proper lens for reshaping the altered corneas. The cornea curvatures of these altered corneas are quite irregular, not measurable, or flattened artificially at the central portion of the cornea. It would be difficult to measure or to apply the conventional cornea information, such as cornea curvatures or eccentricity value of the altered cornea, for preliminary cornea reconstruction to custom make the Ortho-K lenses.

For example, conventional Ortho-K contact lenses with a longer central radius of curvature than the central radius of the cornea are known to change the shape of the cornea by compressing the surface at its apex. This reshaped cornea has a lengthened radius of curvature in its central zone, which serves to improve myopia. However, on an altered cornea of post refractive surgery, it would be very difficult to figure out a lens that can compress the dimpled central portion of the altered cornea for increasing or furthering myopia reduction. It is especially true if the original cornea has already been ablated a lot to correct high myopia as that of higher than −8 or −10 diopters. The higher the original myopia the more cornea tissue will be removed during the refractive surgery, and hence more likely to have postoperative vision problems.

Ortho-K has been performed in one form or another since the early 1970s. Almost all the lenses are designed to mold normal, regular corneas that are parabolic in shape. Modern Ortho-K lenses are usually designed to precisely match the cornea surface by obtaining information from cornea measurement. The measured information, such as cornea curvatures and eccentricity value, is then put into mathematical calculation, known as "preliminary cornea reconstruction," which in turn forms the basis for figuring out lens specifications for manufacturing. It was thought very difficult to figure out the precise lens specifications for molding the altered corneas that are flattest at center portion of the cornea (post-refractive surgery), or abruptly protruded cornea (Keratoconus). Some practitioners have applied the conventional Ortho-K lenses, "trial-and-error," method (piece-by-piece) trying to mold the altered corneas, but are rarely successful. It would be worthwhile to provide a non-surgical method to mold the altered corneas by Ortho-K, which will save the requirement of enhancement operation or corneal transplantation.

The upper limit of Orthokeratology has been thought to be −6.00 diopters. Although it is possible to reduce myopia up to −10.00 diopters by the lens design disclosed in my U.S. Patent, No.: 6,543,897, it is still useful to figure out a contact lens that will further mold the altered cornea by previous Ortho-K to achieve further Ortho-K reduction in excessive high myopia. The difficulty of furthering reduction on the altered cornea of previous Ortho-K is quite similar to that of enhancing the altered cornea of post refractive surgery for adding on myopia reduction.

U.S. Pat. No. 5,963,297 to Reim and U.S. Pat. No. 5,349,395, No. 4,952,045, No. 5,191,365, No. 6,010,219 to Stoyan disclose Ortho-k lens designs for myopia reduction. There has been no disclosure of lenses specifically designed for reshaping the altered corneas. Notwithstanding the improvements provided by modern Orthokeratology for myopia, there remains a need for a contact lens that can be used for effective Ortho-K treatment of altered corneas to restore useful vision by a non-surgical way, thus avoiding the enhance operation or cornea transplantation.

SUMMARY OF THE INVENTION

It is an object of the present invention to provide an Ortho-K contact lens that provides effective molding to the geometrically specific corneas for improving or restoring vision.

It is another object of the present invention to provide an Ortho-K contact lens that provides molding to the centrally protruded corneas such as those due to Keratoconus.

It is yet another object of the present invention to provide an Ortho-K contact lens that provides molding to the centrally dimpled corneas such as those due to post refractive surgical ablation.

It is yet another object of the present invention to provide an Ortho-K contact lens that provides further molding to the centrally flattened corneas such as those due to post myopia Ortho-K to achieve further myopia reduction.

It is yet another object of the present invention to provide an Ortho-K contact lens that provides further molding to the centrally steepened corneas such as those due to post hyperopia Ortho-K to achieve further hyperopia reduction.

The objects of the present invention are achieved by providing an apparatus and method for molding the altered corneas in a patient's eye. In accordance with a method of the present invention, a contact lens is fitted to a cornea of a patient's eye, the contact lens comprising an Optical zone, an Conformation zone, a connecting zones complex, an Alignment zone and the Peripheral zone. The Conformation zone is carefully created to conform to the specific geometry of the altered cornea for correcting the mathematical bias caused by abruptly protruded, or dimpled, portion of the cornea. The Conformation zone may be steeper, or flatter, than the optical zone and works together with the optical zone to mold the central portion of the cornea, which will smooth out the protruded cone of Keratoconus, or correct residual refractive errors of astigmatism, hyperopia or myopia postoperatively. The concept of "adjusting the vaulting," or "adjusting the bearing," relationship of the contact lens by a Conformation zone, without altering the original curvatures of the bearing surfaces, to exert consistent and effective force for cornea molding" is a novel concept, which offers a precisely curved lens for molding the altered cornea, and which is different from just selecting trial lenses empirically by trial-and-error. This novel concept is hereby termed as "conformed molding" for reshaping the geometrically protruded or ablated altered corneas.

In accordance with one embodiment of the present invention, a contact lens is provided, which comprises a base curve portion of the lens, an Conformation curve portion of the lens circumscribing and coupled to the base curve portion, a Connecting curves complex portion of the lens circumscribing and coupled to the Conformation curves portion, and an Alignment curve portion of the lens circumscribing and coupled to the Connecting curves complex portion, and a Peripheral curve portion of the lens circumscribing and coupled to the Alignment curve portion.

The goal of this type of lenses is to mold the altered cornea to smooth out the irregular cone surface of Keratoconus, to flatten the already-flattened central portion of the cornea for further myopia reduction, or to steepen the already flattened central portion of the cornea for counteracting the iatrogenic hyperopia. This type of lenses can also be applied for continuation of the previous Ortho-K treatment of excessive myopia to achieve an add-on myopia reduction, based upon the already-flattened central portion of the altered cornea by Ortho-K. This type of lenses can also be applied for continuation of the previous Ortho-K treatment of excessive hyperopia to achieve an add-on hyperopia reduction, based upon the already-steepened central portion of the altered cornea by Ortho-K.

For treating the altered cornea, the original, or hypothetical, cornea of parabolic curvature is determined by the pre-operative record, or by a carefully calibrated standard trial contact lens set, of which the lens depth is well known. The hypothetical cornea with parabolic surface could be looked upon as having a same volume with the altered cornea covered under the lens. The only difference of the volumes between the hypothetical and the altered corneas is the "tear pool", which means the central dimple of the altered cornea as that of post refractive surgical or post Ortho-K corneas, or the tear pool surrounding the protruded cone of Keratoconus.

The volume of the altered cornea is estimated based on that of the hypothetical cornea and its tear pool. The lens, thus designed, can then be used to conform the altered cornea by transforming the difference of tear pool into the curvature of the Conformation zone. The Conformation zone can then be looked upon as part of the optical zone, and actually it could be a continuous spherical or aspheric curve coupled with positive or negative "e value", according to the type and amount of the tear pool to be conformed.

BRIEF DESCRIPTION OF THE DRAWINGS

FIG. 1 is a side schematic outline view of an ortho-k contact lens 10a according to the present invention for use with an altered cornea of post refractive surgery of a patient's eye. FIG. 1a shows a standardized trial contact lens 10h used for estimating the altered cornea.

FIG. 2 is a side schematic outline view of an ortho-k contact lens 10b according to the present invention for use with an altered cornea of Keratoconus of a patient's eye. FIG. 2a shows a standardized trial contact lens 10h used for estimating the altered cornea.

FIG. 5 is a side view of the ortho-k contact lens according to another embodiment of the present invention for molding the altered cornea of Keratoconus, or of previous hyperopia Ortho-K, with a base curve being steeper than the central curvature of the hypothetical cornea.

FIG. 6 is a front view of the ortho-k contact lens of FIG. 5.

DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims. Additionally, reference have made to my previous U.S. Pat. Nos. 6,361,169, 6,543, 897, and 6,652,095, which are incorporated by reference as if fully set forth herein.

Figure 3:
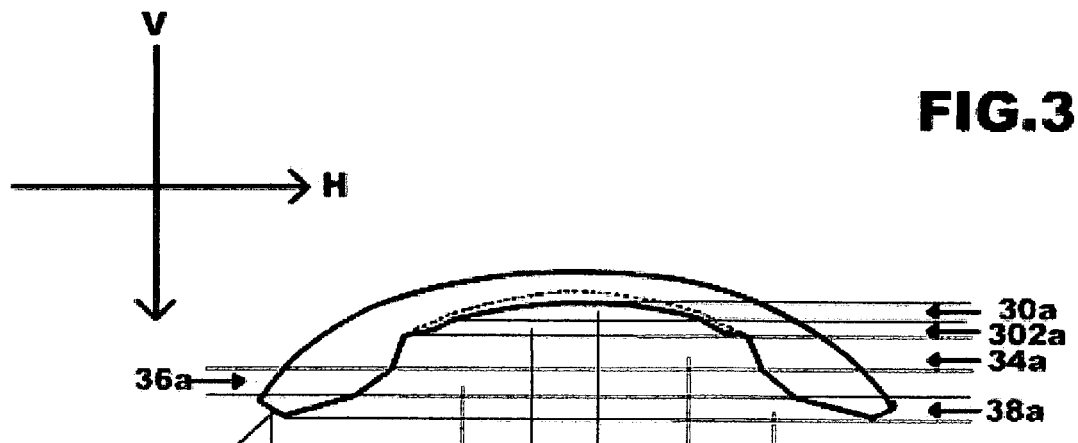
FIG. 3 is a side view of the ortho-k contact lens according to one embodiment of the present invention for molding of the altered cornea of post refractive surgery, of previous myopia Ortho-K, or of Keratoconus, with a base curve being flatter than the central curvature of the hypothetical cornea.
Figure 4:
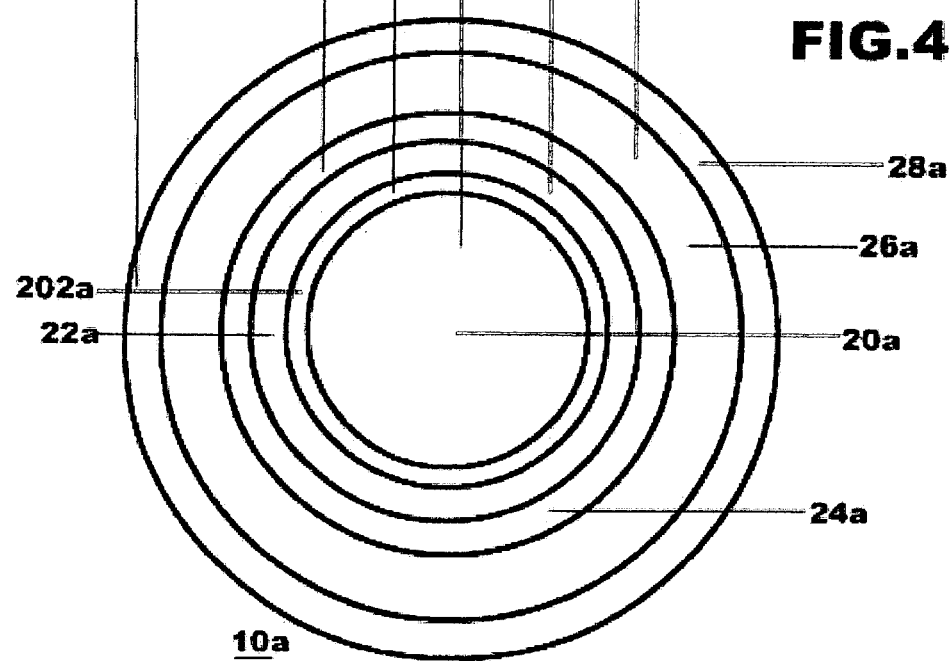
FIG. 4 is a front view of the ortho-k contact lens of FIG. 3.

FIGS. 1, 3, 4 illustrate an ortho-k contact lens 10a according to one embodiment of the present invention. As shown in FIGS. 1 and 1a, the contact lens 10a is a centrally conformed contact lens that is adapted to be worn over the altered cornea 12a, which is estimated by the standardized trial contact lens 10h to have a hypothetical cornea 12h of a patient's eye 14. The contact lens 10a preferably has six correction zones, listed from the center of the lens 10a to the outer periphery: an optical zone 20a, a conformation zone 202a, a connecting zones complex 22a–24a, an alignment zone 26a, and a peripheral zone 28a.

Optical Zone 20

Referring to FIGS. 3–6, the optical zone 20(a, b) has a curvature that is defined by the base curve 30(a, b). The optical zone 20(a, b) is responsible for the corrective steepening of the central portion of the altered cornea 12a of post refractive surgery, and for flattening (or smoothing out) of the central portion of the altered cornea 12b of Keratoconus, during treatment. The radius of curvature of the base curve 30(a, b) can be steeper (i.e. shorter radius) than a measured curvature of a central portion of the altered cornea 12a for relieving over treated hyperopia, or can be flatter (i.e. longer radius) than a measured curvature of a central portion of the altered cornea 12a to eliminate residual myopia. It may also be just any arbitrary curvature that is equal to or steeper (shorter radius) than the central curvature of the hypothetical cornea 12h, but is flatter (longer radius) than the central curvature of the altered cornea 12b for smoothing out the irregular cornea surface in Keratoconus of the altered cornea 12b. However, the radius may also be flatter than the hypothetical cornea 12h to eliminate the axial myopia of the altered cornea 12b of Keratoconus at the same time.

The lens optical zone 20a (LOZ) is preferably created equal to, or slightly smaller than, the cornea optical zone (KOZ) of the altered cornea 12a of post refractive surgery. The purpose of creating a smaller LOZ herein, is to fit it into the surgically ablated KOZ for molding. On the other hand, the optical zone 20b is preferably created equal to or larger than the diameter of the protruded cone in the altered cornea 12b of Keratoconus, but sometimes an optical zone 20b smaller than the cone is acceptable for the very extensive globus cone of the cornea 12b. The purpose of a larger optical zone 20b is to accommodate the cone underneath the optical zone for molding.

The definition of the central curvature of the hypothetical cornea 12h is a novel concept, in comparison to conventional teaching. Lens designers usually relied on the cornea curvature measurable by the keratometric devices as the information for designing lenses. That's the reason why the altered cornea 12a, and 12b were seldom thought moldable by Ortho-K and remained unexplored. The cornea tissue volume and the tear pool underneath the dome of a properly selected trial contact lens 10h can be looked upon as an integral whole to figure out the central curvature of the hypothetical cornea 12h. Three factors, namely, the tear volume of the tear pool, the tissue volume of the altered cornea 12a or 12b underneath the trial contact lens 10h, and the volume of the hypothetical cornea 12h, are mathematically interrelated in terms of sagittal depth, which can be used for figuring out the contact lens 10a, or 10b to mold the altered corneas 12a or 12b, respectively. I will discuss about the relationship later on. This hypothesis firms up the basis for reconstructing the altered cornea 12a, or 12b to quite a reliable reference point and obtain the cornea curvatures before cornea alteration, which is called hereinafter "the hypothetical cornea" 12h. The standardized contact lens used for estimating the hypothetical cornea 12h is called hereinafter "the trial contact lens" 10h.

A series of standardized trial contact lens 10h that are carefully calibrated according to the lens sagittal depth (LSD) and sorted by the reference system, as disclosed in my previous U.S. Pat. No. 6,361,169, can be used as a trial set to probe the altered cornea 12(a, b). From that, we can determine the curvatures of the central, as well as the peripheral, portions of the hypothetical cornea 12h. The set is created according to the shapes of common human eyes so that tracing back to determine the curvatures of the hypothetical cornea 12h will be quite easy and reliable. The procedure would be much easier if the cornea information before cornea alteration is available for selecting a proper trial contact lens 10h. The central dimple in altered cornea 12a (or the surrounding tear pool in altered cornea 12b), plus the volume of the altered cornea 12a (or 12b), can be looked upon as an integral whole, which can then be verified and adjusted as usual to observe the fluorescent patterns of conventional Ortho-K. Some contact lens practitioners may be experienced in selecting conventional RGP for an altered cornea by verifying fluorescent patterns, such as "three point touch method" for fitting Keratoconus. The goal of this invention is to reshape the altered cornea 12a, or 12b by the contact lens 10a, or 10b, respectively, to improve the bare vision or spectacle vision temporarily after removal of the contact lenses 10a, or 10b. This is quite different from the purpose of conventional contact lenses, which are useful only when the contact lenses are worn on the altered cornea. The procedure of trial-fit by the standardized trial contact lens 10h is only a preliminary procedure to estimate the curvatures of the hypothetical cornea 12h for figuring out the specifications for manufacturing contact lens 10a or 10b.

Referring to FIGS. 1, 3 and 4, the curvature of Optical zone 20a, which is the base curve 30a, for molding the post refractive surgical altered corneas 12a can be determined as usual for molding a normal cornea by apical Keratometric readings and targeted power disclosed in previous wisdom. The apical Keratometric readings herein are measured central curvatures from the altered cornea 12a by any reliable keratometric devices as the usual way for fitting conventional Ortho-K, but are usually preferably obtained from topography. The targeted power would be the amount of "residual myopia" or "over treated hyperopia" in conjunction with some over treated power to ensure molding. The base curve 30a can be flatter (longer radius), equal to or steeper (shorter radius) than the central portion of the altered cornea 12a for achieving different purposes. The base curve 30a will be flatter than the curvature of the central portion of the altered cornea 12a if the purpose is to mold a residual myopia. In contrary, the base curve 30a will be steeper than the curvature of the central portion of the altered cornea 12a if the purpose of the contact lens 10a is to mold an over treated hyperopia.

The conventional method of fitting a specific RGP contact lens for Keratoconus is to create a very steep optical zone to vault the cone apex as a cap, followed by a relatively much flatter peripheral curvature to fit the altered shape of the cornea 12b instead of molding it. The method in accordance with the present invention molds the protruded cones back to the original curvatures, or into an ablation like cornea with a flatter central curvature to correct "axial myopia" simultaneously, or into a less protruded regular surface for improving the spectacle vision.

Referring to FIGS. 1, 3, 4, and 2, 5, 6, the curvature of optical zone 20(a, b), which has the base curve 30(a, b), for reshaping the altered cornea 12b of Keratoconus can be determined in two different ways. The first one, for milder Keratoconus with the off-centered cone, is to set up the base curve 30a of the contact lens 10a flatter than the central curvature of the hypothetical cornea 12h for targeting a zero power (known as "emmetropia") after treatment, which should be able to mold the protruded cone back to the original curvatures of the hypothetical cornea 12h, or even turning the protruded altered cornea 12b into an ablation like altered cornea 12a. The altered cornea 12b after molding will become the flattest at the central portion of the cornea, and all the axial myopia could be eliminated simultaneously to restore a relatively good bare vision after removal of the contact lens 10a. However, the base curve 30a cannot be determined by the usual way for molding normal corneas, since the central curvature of the altered cornea 12b is usually irregular or not measurable, hence unreliable to be used for lens design. Instead, the base curve 30a of the contact lens 10a can be easily determined mathematically by the base curve of the trial contact lens 10h and the over refracted power by the well known rule of tear lens effect in fitting conventional RGP.

The second method, for the advanced and severe Keratoconus, is to determine a base curve 30b of the contact lens 10b, arbitrarily with a curvature that is equal to or slightly steeper than the central curvature of the hypothetical cornea 12h aforementioned. The most common way is to determine the base curve 30b to be the mean value of the central curvature of the altered cornea 12b and that of the hypothetical cornea 12h for the first pair. The function of the optical zone 20b now is to offer a space that may accommodate the extensively protruded cone in severe Keratoconus and exerts gentle force on contact surface of the central portion of the altered cornea 12b to mold it into a relatively regular surface for better spectacle vision after removal of the contact lens 10b. The optical zone width 20b should be designed equal to or larger than the widest cone width determined by topography, by which the cone will be securely covered underneath the optical zone 20b of contact lens 10b.

There could be alternatives to the spherical curvatures of optical zone 20(a, b), which could be an aspheric curvature with plus or minus eccentricity value, or divided into several concentric spherical or aspheric curvatures to merge with the conformation zone 202(a, b) outward.

In one embodiment of the present invention, the diameter of the optical zone 20(a, b) ranges from 3 mm to 8 mm, and the radii of the curvature for the base curve 30(a, b) ranges from 15.0 mm to 5.0 mm.

Conformation Zone 202(a, b)

Referring to FIGS. 3, 4, 5 and 6, the Conformation zone 202(a, b) has a radius of curvature defined by a predefined conformation curve 302(a, b), which is carefully calculated to conform the lens optical zone 20(a, b) of the contact lens 10a, or 10b, to bear on the central portion of altered cornea 12a, or 12b, to mold it into a flatter, steeper or a relatively regular surface, respectively. The conformation curve 302(a, b) of the conformation zone 202(a, b) may be flatter (longer radius), or steeper (shorter radius) than or equal to the base curve 30(a, b), according to the type of the altered cornea 12a, or 12b, to be reshaped.

Molding Post Refractive or Ortho-K Cornea

Reference is made to FIGS. 3 and 4. In designing the contact lens 10a for molding the post refractive surgical or the post Ortho-K altered cornea 12a, the conformation zone 202a could be looked upon as a hooking arm of the steeper outer connecting zones complex 22a–24a, to bear the optical zone properly on the central portion of the altered cornea 12a. Whilst summation of the zone width of the optical zone 20a and the conformation zone 202a should be designed nearly equal to or slightly smaller than the surgically ablated or Ortho-K molded optical zone for the optical zone 20a of the contact lens 10a to mold the central dimple of the altered cornea 12a effectively.

The ablated optical zone can be estimated by measuring the cornea topography. The hypothetical cornea 12h offers us a reference point for estimating the dimple depth to be conformed, which theoretically equals to the sagittal depth difference, within the scope of the ablated optical zone width, between the central curvature of the hypothetical cornea 12h and that of the altered cornea 12a in reshaping residual myopia, or the difference between the central curvature of the hypothetical cornea 12h and that of the contact lens 10a in reshaping over treated hyperopia. The dimple depth could then be subtracted from the sagittal depth of the hypothetical cornea 12h to figure out the sagittal depth of the contact lens 10a.

The conformation curve 302a of the contact lens 10a could then be figured out, which is usually flatter than the outer connecting curves 34a–36a to form a centrally hooking portion, of which the bending angle is conforming precisely to eliminate the aforementioned tear dimple. Thus, the sagittal depth within the scope of the ablated or Ortho-K molded dimple zone is now successfully transformed into a suitable conformation zone 202a and its curvature 302a to form the centrally hooked portion connected to the outer connecting zones complex 22a–24a, which allows the optical zone 20a to bear on the central portion of the altered cornea 12a for effective molding. All the mathematical terms herein are based upon the well-known method for sagittal depth calculation of a contact lens.

On the lens 10a for molding post Ortho-K residual myopia, post-refractive surgical residual myopia, or overtreated hyperopia of the altered cornea 12a, the conformation zone 202a may preferably be flatter than the outer connecting zones complex 22a–24a to hook and bend the optical zone 20a of the contact lens 10a so as to cause a bearing on the dimple portion of the altered cornea 12a.

There could be alternatives to the structures of the conformation zone 202a and conformation curve 302a for achieving the "bending" of the optical zone 20a. The conformation zone 202a may be divided into several adjacent flatter and steeper curvatures, as long as the total "bending angle" is kept the same. It would be of no matter what interweaving shape the "hook" may be. The curve may also be substituted by an aspheric curvature to merge with the optical zone 20a to form a continuously and gradually flattening curvature with certain e-value, the "self bending" surface, or to merge with the connecting zones complex 22a–24a to become part of the zones complex. The main task herein is to acquire a precisely estimated "bending effect" of the conformation zone 202a, by the aforementioned principles, to bear the central portion of the contact lens 10a on the dimple portion of the altered cornea 12a for proper reshaping.

Molding Keratoconus Cornea

Before designing the contact lens 10b for molding the altered cornea 12b of Keratoconus, we have to know the surface map of common Keratoconus. The protruded cones are usually located inferior to, or below, the geometric center of the altered cornea 12b, forming an abruptly steepened boundary just below the geometric center of the altered cornea 12b, above which the cornea surface is usually flattened forming a highly contrasting interface. The off centered cone of the altered cornea 12b of Keratoconus can then be looked upon as the edge of a semi-ablated cornea surface, in light of the flatter (central and upper) portion of the cornea adjacent to the protruded cone. There may also be a dimpled tear pool underneath the optical zone of a properly selected trial contact lens 10h. The aforementioned skills used to figure out the conformation zone 202a and its curvature 302a for the altered cornea 12a (of post refractive surgery) are all applicable in designing the contact lens 10a, for molding the off centered cone of the altered cornea 12b. If properly designed, the contact lens 10a will expand and smooth out the flatter portion of the cornea adjacent to the off centered cone and create an effective cornea optical zone for better bare vision. However if the protruded cone is located or has been molded into a shape located at the central portion of the altered cornea 12b, there would be no conformation zone 202a or conformation curvature 302a needed in designing the contact lens 10a for molding on the steeper portion of the central cone, by a very flat optical zone 20a.

The hypothetical cornea 12h now offers a reference point for estimating the original sagittal height of the altered cornea 12b by the trial contact lens 10h, and the approximate cornea curvatures before cone protrudes. To achieve the purposes of molding and reshaping the protruded cone or to smooth out the highly contrasting interface to improve the correctable vision, by the assigned optical zone 20a and its curvature 30a, the contact lens 10a should be created with a precisely conformed sagittal height that may exert dual forces simultaneously on the central portion of the altered cornea 12b by the optical zone 20a, as well as on the mid-peripheral portion of the altered cornea 12b by the alignment zone 26a, for effective cornea molding. The central portion of the altered cornea 12b will be molded into an ablation like smooth surface by the optical zone 20a of the contact lens 10a, with a base curve 30a that is flatter than the central curvature of the hypothetical cornea 12h.

The way to figure out the conformation zone 202a and its curvature 302a, for bending the optical zone 20a beyond the cone to bear on the flatter central and upper portion of the altered cornea 12b, is quite similar to the aforementioned way of hooking and bending the optical zone 20a on the altered cornea 12a. However, since only lower portion of the cornea is steeper (protruded) instead of a ring shaped steepening in the altered cornea 12a, only part of the estimated bending amount, by and large, about 50%, of it should be conformed. The outer portion of the lens structure next to the conformation zone 202a is determined according to the shape of the hypothetical cornea 12h. The conformation curvature 302a is usually flatter than the central base curve 30a, where the bending angle is conformed precisely to eliminate the tear dimple aforementioned. The method according to the present invention offers a methodology to conform the reverse geometric contact lens disclosed in my previous U.S. Pat. No. 6,652,095, by figuring out the conformation zone 202a and conformation curvature 302a to match the lens for better molding of the altered cornea 12a.

In some situations, the contact lens 10a may be tented up at the lower portion of alignment zone 26a if the cone is quite extensive and more peripheral, which may weaken the peripheral compression of the dual forces for effective molding of the altered cornea 12b. That's the reason why, for the very advanced or even the severe cone, we may have to assign the base curve 30b to be equal to or steeper than the central curvature of the hypothetical cornea 12h to match the altered cornea 12b, of which the conformation zone 202b can be looked upon as an up-stretching arm connected to the adjacent flatter connecting zones complex 22b–24b, bearing the optical zone 20b gently on the protruded portion of the altered cornea 12b. Any increment in steepness (shortening radius) of the base curve 30b, by a curvature between the flatter central curvature of the hypothetical cornea 12h and the steepest curvature of the cone apex of the altered cornea 12b, may tent up the optical zone 20b as well as increasing the tightness of the contact lens 10b.

The sagittal height, which will be increased by the steepened base curve 30b, can be estimated quite precisely according to two factors, namely the amount of increment in steepness (decrement in radius) of the base curve 30b from the central curvature of the hypothetical cornea 12h, and the position of the cone apex off centered from the geometric center of the altered cornea 12b. The methodology in accordance with the present invention offers a method to conform the dual geometric ("DG") contact lens disclosed in my previous patent, U.S. Pat. No. 6,543,897, by figuring out the conformation zone 202b and conformation curvature 302b to conform the lens for better molding of the altered cornea 12b.

To learn the skills of conforming the dual geometric contact lens for molding the altered cornea 12b herein is preferably started from a centrally located cone of Keratoconus, or the steepened cornea after hyperopia Ortho-K, with a base curve 30b matching to the central curvature of the hypothetical cornea 12h. The hypothetical cornea 12h can be looked upon as a neutral point. Thus these three geometric centers of the hypothetical cornea 12h (neutral point), that of the altered cornea 12b, and that of the contact lens 10b will be coaxial theoretically. Any increment in the steepness (decrement of radius) of the base curve 30b, will add sagittal height to the optical zone 20b, also to the height of the contact lens 10b, so that the contact lens 10b will be tented up for that amount coaxially. The increased sagittal height, within the scope of the optical zone 20b, can be figured out and subtracted from the total lens height of the contact lens 10b, by figuring it into the conformation curvature 302b, which is usually flatter than the base curve 30b, to restore the original bearing relationship of the optical zone 20b on the central portion of the altered cornea 12b.

In higher hyperopia situations, the altered cornea 12b of post previous hyperopia Ortho-K by dual geometric lenses (as described in my previous U.S. Pat. No. 6,652,095), may have residual refractive errors resulted from a centrally flattened area (known as a "central lake"), which is caused by the residual vaulting space underneath the steeper optical zone of the said dual geometric contact lens. The residual vaulting space underneath the optical zone 20b of the contact lens 10b can be diminished or eliminated by incorporating the aforementioned conformation zone 202b to restore the contact relationship of optical zone 20b to bear on the central portion of the altered cornea 12b for add-on hyperopia reduction. The amount to be conformed is usually set to be about 50% of the initial vaulting underneath the said dual geometric lens (as described in my previous U.S. Pat. No. 6,652,095) for hyperopia molding, but may also be determined individually according to different zone widths of the "central lake" on the altered cornea 12b after molding, which can be easily determined by modern topography.

In most situations, the cones of the Keratoconus are seldom located right on the geometric center of the altered cornea 12b, but are usually decentered inferiorly. The bearing point, on the altered cornea 12b, of the contact lens 10b will be also off centered inferiorly to the same extent, The way to estimate the conformation zone 202b and conformation curve 302b would be quite different from the coaxial cone aforementioned. The off centered cone will form some tear space underneath the central portion of the contact lens 10b. There will be also raised edge at lower portion of the contact lens 10b accordingly.

Any increment in steepness (decrement in radius) of the base curve 30b over the central curvature of the hypothetical cornea 12h, will further tent up the optical zone 20, and increase the tear height underneath the central portion of the contact lens 10b as aforementioned. However for an off centered cone, the increment in steepness of the base curve 30b will also shift the initially off centered bearing point on the contact lens 10b closer to the geometric center of the optical zone 20b, and hence substantially diminish the central tear height inversely. The net increment of the tear height due to the steeper base curve 30b could then be determined by these two inversely related factors and figured into the conformation curvature 302b of the contact lens 10b to offset the increased central tear height and bear the optical zone 20b properly on the protruded portion of the altered cornea 12b for effective reshaping.

The inverse effect of decrement in central tear height with a steeper base curve 30b is positively related to the off centering distance of the cone. For better understanding, if the cone apex is supposedly located right at the outmost margin of the optical zone of the trial contact lens 10h, the lens center will be significantly tented up due to the totally off centered cone. Any increment in the steepness of the base curve 30b of the contact lens 10b will not really increase (0% increment) in the central tear height, but should be 100% offset innately due to the totally off centered cone until the increment of the steepness of the base curve 30b reaches the curvature of the cone apex. There won't be any conformation zone 202b or its curvature 302b needed to mold the totally off centered cone. In another word, the contact lens 10b for a totally off centered cone will be self-conformable. The optical center of the contact lens 10b, with increasing steepness of the base curve 30b, will reposition itself slightly off centered moving closer to the cone apex of the altered cornea 12b. The initially lifted edge of the contact lens 10b will be also less elevated accompanying the self-conformation of the contact lens 10b. On the other hand, any increment in the steepness of the base curve 30b will be 100% reflected in the increment of the central tear height underneath the contact lens 10b with a centrally located cone as aforementioned. The conformation zone 202b and conformation curve 302b should then be created to offset the increased central tear height for bearing the optical zone of the contact lens 10b properly on the altered cornea 12b. The inverse effect of diminishing (decrement in) central tear height accompanying a steeper base curve 30b, in between these two ends of cone positions above mentioned, will be positively related to the radial distance measured from the geometric center of the altered cornea 12b to the outmost portion of the cone by topography.

Generally speaking, the main purpose of the conformation zone 202b in the contact lens 10b for managing Keratoconus is to offset the sagittal height that is tented up accompanying the increment (decrement in radius) of the steepness of the optical zone 20b, to restore the central bearing relationship of the optical zone 20b on the cone apex of the altered cornea 12b for effective molding by dual forces. The amount of the sagittal height to be offset can be figured out mathematically according to three variables of:

1) The sagittal height of the optical zone 20b with a base curve 30b steeper than the central curve of the hypothetical cornea 12h;

2) The sagittal height of the hypothetical cornea 12h within the scope of the optical zone 20b;

3) The off center radial distance of the cone apex from the geometric center of the altered cornea 12b;

The sagittal difference between (1) and (2) should be adjusted by factor (3) to acquire the sagittal height to be offset by the conformation zone 202b, which can be transformed into the conformation curvatures 302b by well known mathematical rules for sagittal depth calculation. The factor (3) is usually set to be about 50% of the total sagittal height to be conformed. The reason is, most of the time the cone usually locates just below the geometric center of the altered cornea 12b and the optical zone 20b is usually set to be equal to or only slightly larger than the cone width as aforementioned. Thus the cone apex will locate at about half way (50% off center distance) of the optical zone 20b. That is to say, by and large, about 50% of the sagittal depth difference between (1) and (2) could be conformed innately by the 50% off centered cone, and the remaining 50% of the increased tear depth should be compensated by the conformation zone 202b and the conformation curve 302b.

On the other hand, for smaller central cones, the contact lens 10a with a base curve 30a flatter than the central curvature of the hypothetical cornea 12h can be used to mold the altered cornea 12b into another altered cornea 12a forming an ablation like surface as aforementioned. It is actually possible firstly to use the conformed contact lens 10b to mold an off centered advanced or sever cone into a smoother central cone, followed by a consecutive contact lens 10a with flatter optical zone 20a to further reshape the altered cornea 10b into another altered cornea 10a with an ablation like central curvature to achieve crisp bare vision.

If the base curve 30a is assigned flatter than the central curvature of the hypothetical cornea 12h for smoothing out the high contrast interface and relieving the axial myopia as well, the conformation zone 202a and curvature 302a will be usually assigned flatter than the outer connecting curves 34a–36b to hook and bend the optical zone 20a over the cone to bear the optical zone 20a of the contact lens 10a on the flatter upper portion of the alter cornea 12b. On the other hand, if the base curve 30b is assigned steeper than the central curvature of the hypothetical cornea 12h, the conformation curvature 302b will be flatter than the base curve 30b to form an adaptation arm, of which the angle can be precisely figured out by aforementioned three factors. Thus, with the help of conformation zone 202b and its curvature 302b, the properly conformed contact lens 10b will be able to bear on the protruded cone gently by the optical zone 20b, as well as to compress on the peripheral portion of the altered cornea 12b by the alignment zone 26b simultaneously for effective molding. All the mathematical terms herein are based upon the well-known formula for sagittal depth calculation, but are limited to the scope of the optical zone 20b and the conformation zone 202b.

There could be alternatives to the structures of the conformation zone 202b and conformation curve 302b for offsetting the vaulting of the optical zone 20b. The conformation zone 202b can be divided into several successively flatter and steeper curvatures, as long as the total "bending or offsetting angle" or "bending or offsetting amount" is kept the same. It would be of no matter what interweaving or intermediate shape the conformation zone 202b may be. The conformation curve 302b may also be flattened to such an extent that it becomes zero or minus in power (diopters), which is actually a plane surface or convex in shape defined mathematically. The curve may also be substituted by an aspheric curvature to merge with the optical zone 20b to form a continuous and gradually flattening curve with a positive e-value, the "self bending or offsetting" surface, or to merge with the inner connecting zone 22b to become part of the connecting zones complex 22b–24b. The only requirement is always keeping a proper "bending or offsetting effect" by the conformation zone 202b and its curvature 302b to allow the optical zone 20b to compress on the central portion, and to allow the alignment zone 26b to compress on the peripheral portion of the altered cornea 12b.

In one embodiment of the present invention, the diameter of the conformation zone 202(a, b) ranges from 0.1 mm to 3.0 mm. The radius of curvature for the conformation curve 302(a, b) is 1–60 diopters flatter (longer radius) than the base curve 30b in a conformed contact lens 10b or 1–60 diopters flatter (longer radius) than the outer connecting curves 34a–36a in contact lens 10a for different contact lens 10a or 10b.

Although the present invention illustrates the provision of one conformation curve 302(a or b), it is also possible to provide the contact lens 10(a or b) with two or more conformation zones and curves, as well as substitute the zone with an aspheric curve of certain e-value, or even merge with connecting zones complex 22–24(a or b) to form a continuously flatter or steeper curvature connecting to the optical zone 20(a or b).

Connecting Zones Complex 22–24(a or b)

Referring to FIGS. 3–6, the connecting zones complex 22–24(a or b) acts as a transition region, compression surface, or tear circulation zone between the conformation zone(s) 202(a or b) and the alignment zone 26(a or b). The connecting zones complex 22a–24a for contact lens 10a may be considered a combination of the Fitting zone and Facilitate zone disclosed in my aforementioned U.S. Pat. No. 6,543,897, and the connecting zones complex 22b–24b for contact lens 10b may be considered a combination of the Plateau zone and Fitting zone disclosed in the aforementioned U.S. Pat. No. 6,652,095. However, the sagittal depth of the connecting zones complex 22–24(a or b), in accordance with the present invention, is determined by the estimated hypothetical cornea 12h, so that the Alignment zone 26(a or b) will bear on the peripheral cornea properly before and after molding.

Alignment Zone 26(a or b)

Referring to FIGS. 3–6, the alignment zone 26(a or b) is designed to provide and maintain centration of the lens 10(a, b) by having a radius of curvature that is either the same as, or slightly longer than the central curvature of the hypothetical cornea 12h (i.e., to match the peripheral cornea). A predefined alignment curve 38(a or b) defines the curvature of the alignment zone 26(a or b), which is almost the same as the hypothetical curvature of the portion of the cornea 12h circumscribing the central portion of the cornea 12h.

The alignment zone 26(a or b) creates a large bearing area 40 in a region corresponding with the portion of the altered cornea 12a, 12b where a centering force is created that maintains the optical zone 20(a or b) substantially at the apical center of the altered cornea 12a, 12b. The alignment curve 38(a or b) is determined by the hypothetical central K, which is estimated by the aforementioned trial contact lens 10h.

The associated alignment curve 38(a or b) creates a bearing zone over a large surface area of the altered cornea 12a, 12b, which is helpful in aligning the lens 10a, 10b at the apex of the altered cornea 12a, 12b. The alignment zone 26(a or b) and its curve 38(a or b) has been disclosed in the aforementioned U.S. Pat. Nos. 6,543,897, and 6,652,095.

Alternatively, the alignment zone 26(a or b) can be segmented into multiple curves and any combination of any shapes or curves, as long as sufficient bearing area is maintained.

Peripheral Zone 28(a or b)

Referring FIGS. 3–6, the peripheral zone 28(a or b) is designed with a radius of curvature longer than that of the cornea 12 (a or b), yielding a curvature less than the estimated curvature of a portion of the hypothetical cornea 12h circumscribing the central portion of the hypothetical cornea 12h that corresponds to the alignment zone 26(a or b). The peripheral zone 28(a or b) has its surface contour defined by a predefined peripheral curve 42(a or b) which has a curvature that nearly parallels the portion of the hypothetical cornea 12h underneath it, but is flatter than the hypothetical cornea 12h. The peripheral zone 28(a or b) promotes tear flow under the contact lens 10a, 10b by taking advantage of a tear pumping action created when the individual blinks the eyelid. This tear flow allows constant lubrication and oxygenation of the lens-cornea interface and results in a more comfortable and wearable lens 10a, 10b.

Additionally, the peripheral zone 28(a or b) is designed to create a slight edge lift which allows easy contact lens removal from the cornea 12a, 12b. The peripheral zone 28(a or b) and its curve 42(a or b) have been disclosed in the aforementioned U.S. Pat. Nos. 6,543,897, and 6,652,095.

The different radii used to define the base curve 30(a or b), the conformation curve 302(a or b), the connecting curves 34(a or b)–36(a or b), the alignment curve 38(a or b)

and the peripheral curve 42(a or b) are calculated after careful examination of the patient's eye and the associated ocular tissue. The corneal curvature must be measured, the proper contact lens power defined, and the anticipated physiological response to the contact lens 10a, 10b must be determined. An individual skilled in the examination techniques of the ocular system is typically capable of performing these tasks.

For example, the contact lens 10a of the present invention can achieve a reduction of residual myopia up to −2.0 diopters post refractive surgery of previous myopia −8.00 D, within a short wearing time of 6–8 hours a day for initial wearing, and 4–8 hours a day to maintain.

Test Lens Kits for Determining a Hypothetical Cornea

In accordance with the present invention, a kit of test lenses can be implemented to help determine a hypothetical cornea for use with post-LASIK and post-myopia Ortho-K amendments. The kit comprises a reference table and a set of trial lenses. The reference table is used to determine a conformation data by using one or more of the following factors:

a) pre-operative or pre-ortho-K KM readings;
b) post-operative or post-ortho-K KM readings;
c) power reduced before and after operation, or before and after ortho-K;
d) post-operative or post-ortho-K cornea optical zone.

The set of trial lenses includes conformed lenses based on the conformation data, in predetermined increments, from the reference table.

Another kit of test lenses can be implemented to help determine a hypothetical cornea for use with Keratoconus and post-hyperopia Ortho-K amendments. The kit comprises a reference table and a set of trial lenses. The reference table is used to determine a conformation data by using one or more of the following factors:

a) KM readings from a set of normal corneas;
b) KM readings of at least one of cone apex and post-hyperopia Ortho-K;
c) either one, or both, of cone widths of Keratoconus or steepened cornea zone of hyperopia Ortho-K;
d) magnitude of off-centering of the cone apex.

The set of trial lenses includes conformed lenses based on the conformation data, in predetermined increments, from the reference table.

It should be pointed out that the use of reference tables, at a general conceptual level for finding normal contact lenses, is already described in my U.S. Pat. No. 6,361,169.

Although the present invention has been described in connection with the preferred embodiments, it will be appreciated by those skilled in the art that modifications can be made and alternatives utilized without departing from the spirit and scope of the present invention.

EXAMPLE

A contact lens having the following dimensions were provided for a AA1125 patient post refractive laser surgery (LASIK), which had been enhanced once due to myopia recurrence:

<Right eye>
Preoperative KM: unavailable
Preoperative refraction: unavailable
Postoperative Sim-K: 39.11 (8.63), 39.63 (8.52)
Postoperative residual myopia: −1.75 diopters (myopia −1.75 diopters)
Central K of hypothetical cornea: 44.75 D (estimated by trial contact lens)
Ablated cornea optical zone: 5 mm
Estimated dimple height to be conformed: 52 microns
Optical zone 20: width 5.0 mm, radius of curvature 9.72 mm
Conformation zone 202: an aspheric curvature merged with optical zone by adding an eccentricity of 0.80 to the base curve
Fitting zone 22: width 0.4 mm, radius of curvature 6.28 mm
Facilitate zone 24: width 0.4 mm, radius of curvature 7.21 mm
Alignment zone 26: width 1.6 mm, radius of curvature 7.70 mm with an eccentricity of 0.40
Peripheral zone 28: width 0.4 mm, radius of curvature 11.00 mm
Lens power: +2.00 with a front eccentricity of +0.42 to compensate for the ADD effect resulted from the eccentricity on base curve <Left eye>
Preoperative KM: unavailable
Preoperative refraction: unavailable
Postoperative Sim-K: 39.93 (8.45), 40.99 (8.23)
Postoperative residual myopia: −1.50–0.50 @ 135 (myopia −1.50 and astigmatism 0.50 diopter)
Central K of hypothetical cornea: 44.75 D (estimated by trial contact lens)
Estimated dimple height to be conformed: 42 microns
Optical zone 20: width 5.0 mm, radius of curvature 9.58 mm
Conformation zone 202: an aspheric curvature merged with optical zone by adding an eccentricity of 0.80 to the base curve
Fitting zone 22: width 0.4 mm, radius of curvature 6.26 mm
facilitate zone 24: width 0.4 mm, radius of curvature 7.18 mm
Alignment zone 26: width 1.6 mm, radius of curvature 7.70 mm with an eccentricity of 0.40
peripheral zone 28: width 0.4 mm, radius of curvature 11.00 mm
Lens power: +2.00 with a front eccentricity of +0.35 to compensate for the ADD effect resulted from the eccentricity on base curve The pair of contact lenses was worn by the patient for 2 days, at 7–8 hours a day. After this correction period, the patient experienced a myopia reduction to zero power. This is equivalent to a myopia reduction of −1.75D (spherical equivalent) for both eyes. The maintenance period (of nearly zero power) lasted for all awakening hours with a 5–7 hour maintenance night wearing. The topography of the cornea is well centered and has a definite flattening of cornea curvature within the ablated central zone to support an efficient reduction in myopia. This case has been followed for six months with no side effects.

What is claimed is:

1. A contact lens for reshaping an altered cornea which has been altered from a pre-altered cornea, said altered cornea having an abruptly protruded portion, said pre-altered cornea having a sagittal height at its central area, defining a hypothetical lens sagittal height, comprising:

a first zone having a curvature defined by a first curve;
a second zone coupled to said first zone and extending radially therefrom, said second zone having a curvature defined by a second curve, such that said second curve alters said hypothetical lens sagittal height according to predetermined conformation data for matching said protruded portion of said altered cornea without altering said first curve.

2. A contact lens of claim 1, wherein said second curve is formed based on predetermined conformation data for said altered cornea.

3. A contact lens for reshaping an altered cornea which has been altered from a pre-altered cornea, said altered cornea having an abruptly protruded portion, said pre-altered cornea having a sagittal height at its central area, defining a hypothetical lens sagittal height, comprising:
   a first zone having a curvature defined by a first curve;
   a second zone coupled to said first zone and extending radially therefrom, said second zone having a curvature defined by a second curve, said second curve being flatter than said first curve, such that said second curve alters said hypothetical lens sagittal height without altering said first curve, wherein said second zone shortens said lens sagittal height to match said first zone for compressing said altered cornea, without altering said first curve.

4. A contact lens for reshaping an altered cornea which has been altered from a pre-altered cornea, said altered cornea having an abruptly protruded portion, said pre-altered cornea having an sagittal height at its central area, defining a hypothetical lens sagittal height, comprising:
   a first zone having a curvature defined by a first curve;
   a second zone coupled to said first zone and extending radially therefrom, said second zone having a curvature defined by a second curve, said second curve being flatter than said first curve, such that said second curve alters said hypothetical lens sagittal height without altering said first curve, wherein said second zone shortens said lens sagittal height to match said first zone for compressing said altered cornea, without altering said first curve, wherein said second curve is formed based on predetermined conformation data for said altered cornea.

5. A contact lens for reshaping an altered cornea which has been altered from a pre-altered cornea, said altered cornea having an abruptly protruded portion, comprising:
   an optical zone having a curvature defined by a base curve;
   a conformation zone coupled to said optical zone and extending radially therefrom, said conformation zone having a curvature defined by a conformation curve, said conformation curve being formed flatter than said base curve;
   a connecting zones complex coupled to said conformation zone and extending radially therefrom, said connecting zones complex having at least a first curvature defining a first curve and a second curvature defining a second curve, said first curve being flatter than said base curve, said second curve being steeper than said first curve;
   an alignment zone coupled to said connecting zones complex and extending radially therefrom, said alignment zone having a curvature defined by an alignment curve, said alignment curve being flatter than said second curve;
   a peripheral zone coupled to said alignment zone and extending radially therefrom, said peripheral zone having a curvature defined by a peripheral curve, said peripheral zone forming an edge lift to act as tear reservoir.

6. A contact lens of claim 5, wherein said base curve is formed steeper than a predetermined central portion of said pre-altered cornea.

7. A contact lens of claim 5, wherein said conformation curve is formed based on predetermined conformation data for said altered cornea.

8. A contact lens of claim 6, wherein said conformation curve is formed based on predetermined conformation data for said altered cornea.

9. A contact lens for reshaping an altered cornea which has been altered from a pre-altered cornea, said altered cornea having an abruptly protruded portion, said pre-altered cornea having a sagittal height at its central area, defining a hypothetical lens sagittal height, comprising:
   an optical-conformation zone having a predetermined e-value to form at least one aspherical base curve based on conformation data of said altered cornea, said e-value being such that it causes the altering of said lens sagittal height without altering the most central portion of said aspherical base curve.

10. A contact lens of claim 9, further comprising:
    a connecting zones complex coupled to said optical-conformation zone and extending radially therefrom, said connecting zones complex having at least a first curvature defined by a first curve and a second curvature defined by a second curve, said first curve being flatter than said base curve, said second curve being steeper than said first curve;
    an alignment zone coupled to said connecting zones complex and extending radially therefrom, said alignment zone having a curvature defined by an alignment curve, said alignment curve being flatter than said second curve;
    a peripheral zone coupled to said alignment zone and extending radially therefrom, said peripheral zone having a curvature defined by a peripheral curve, said peripheral zone forming an edge lift to act as tear reservoir.

11. A contact lens of claim 9, wherein:
    said e-value is determined such that said optical-conformation zone alters said hypothetical lens sagittal height without altering the most central portion of said aspherical base curve.

12. A contact lens for reshaping an altered cornea which has been altered from a pre-altered cornea, said altered cornea having a dimpled central portion, comprising:
    an optical zone having a curvature defined by a base curve;
    a conformation zone coupled to said optical zone and extending radially therefrom, said conformation zone having a curvature defined by a conformation curve;
    a connecting zones complex coupled to said conformation zone and extending radially therefrom, said connecting zones complex having at least a first curvature defining a first curve, said first curve being sleeper than said base curve, said conformation curve being formed flatter than said first curve, said conformation curve being formed such said conformation curve alters said hypothetical lens sagittal height without altering said base curve.

13. A contact lens of claim 12, wherein said conformation curve is formed based on predetermined conformation data for said altered cornea.

14. A contact lens of claim 12, wherein:
    said connecting zones complex further comprises a second curvature defined by a second curve, said second curve is flatter than said first curve.

15. A contact lens of claim 13, wherein:
said connecting zones complex further comprises a second curvature defined by a second curve, said second curve is flatter than said first curve.

16. A contact lens of claim 14, further comprising:
an alignment zone coupled to said connecting zones complex and extending radially therefrom, said alignment zone having a curvature defined by an alignment curve, said alignment curve being flatter than said second curve;
a peripheral zone coupled to said alignment zone and extending radially therefrom, said peripheral zone having a curvature defined by a peripheral curve, said peripheral zone forming an edge lift to act as tear reservoir.

17. A contact lens of claim 15, further comprising:
an alignment zone coupled to said connecting zones complex and extending radially therefrom, said alignment zone having a curvature defined by an alignment curve, said alignment curve being flatter than said second curve;
a peripheral zone coupled to said alignment zone and extending radially therefrom, said peripheral zone having a curvature defined by a peripheral curve, said peripheral zone forming an edge lift to act as tear reservoir.

18. A contact lens of claim 12, wherein said base curve is flatter than a predetermined central portion of said pre-altered cornea.

19. A contact lens of claim 13, wherein said base curve is flatter than a predetermined central portion of said pre-altered cornea.

20. A contact lens of claim 14, wherein said base curve is flatter than a predetermined central portion of said pre-altered cornea.

21. A contact lens for reshaping an altered cornea from a pre-altered cornea, said altered cornea having a dimpled central, said pre-altered cornea having a sagittal height at its central area, defining a hypothetical lens sagittal height, comprising:
an optical zone having a curvature defined by a base curve;
a conformation/first connecting zone having a predetermined e-value to form at least one aspherical conformation/first connecting curve based on conformation data for said altered cornea, said e-value being such that it causes the altering of said lens sagittal height without altering the most central portion of said aspherical base curve.

22. A contact lens of claim 21, wherein:
said e-value alters said hypothetical lens sagittal height without altering said base curve.

23. A contact lens of claim 21, further comprising:
a second connecting zone coupled to said conformation/first connecting zone and extending radially therefrom, said second connecting zone having at least a second curvature defining a second curve.

24. A contact lens of claim 22, further comprising:
a second connecting zone coupled to said conformation/first connecting zone and extending radially therefrom, said second connecting zone having at least a second curvature defining a second curve.

25. A contact lens of claim 23, further comprising:
an alignment zone coupled to said second connecting zone and extending radially therefrom, said alignment zone having a curvature defined by an alignment curve, said alignment curve being flatter than said second curve;
a peripheral zone coupled to said alignment zone and extending radially therefrom, said peripheral zone having a curvature defined by a peripheral curve, said peripheral zone forming an edge lift to act as tear reservoir.

26. A contact lens of claim 24, further comprising:
an alignment zone coupled to said second connecting zone and extending radially therefrom, said alignment zone having a curvature defined by an alignment curve, said alignment curve being flatter than said second curve;
a peripheral zone coupled to said alignment zone and extending radially therefrom, said peripheral zone having a curvature defined by a peripheral curve, said peripheral zone forming an edge lift to act as tear reservoir.

27. A contact lens for reshaping an altered cornea which has been altered from a pre-altered cornea, said altered cornea having a dimpled central portion, said pre-altered cornea having a sagittal height at its central area, defining a hypothetical lens sagittal height, comprising:
a first zone having a curvature defined by a first curve;
a second zone coupled to said first zone and extending radially therefrom, said second zone having a curvature defined by a second curve;
a third zone coupled to said second zone and extending radially therefrom, said third zone having a curvature defined by a third curve, said third curve being steeper than said first curve, said second curve being formed flatter than said third curve, said second curve altering said hypothetical lens sagittal height without altering said first curve.

28. A contact lens of claim 27, wherein said second curve is formed based on predetermined conformation data for said altered cornea.

29. A contact lens of claim 27, wherein said first zone comprises a plurality of sub-first zones, each sub-first zone having a curvature defined by a curve.

30. A contact lens of claim 28, wherein said first zone comprises a plurality of sub-first zones, each sub-first zone having a curvature defined by a curve.

31. A contact lens of claim 27, wherein said first zone comprises an inner and outer zones, said inner zone having an inner curvature defined by an inner curve, said outer zone having an outer curvature defined by an outer curve, said outer curve is flatter than said inner curve.

32. A contact lens of claim 28, wherein said first zone comprises an inner and outer zones, said inner zone having an inner curvature defined by an inner curve, said outer zone having an outer curvature defined by an outer curve, said outer curve is flatter than said inner curve.

33. A contact lens of claim 27, wherein said first curve is flatter than a predetermined central portion of said pre-altered cornea.

34. A contact lens of claim 28, wherein said first curve is flatter than a predetermined central portion of said pre-altered cornea.

* * * * *